United States Patent
Herrmann et al.

(10) Patent No.: US 8,568,630 B2
(45) Date of Patent: Oct. 29, 2013

(54) ROTARY PRESS FOR QUALITY SURVEILLANCE OF POWDERED PRESSED MATERIAL

(75) Inventors: Rainer Herrmann, Hamburg (DE); Udo Schlemm, Hamburg (DE); Ingo Schmidt, Schwarzenbek (DE); Ulrich Arndt, Lauenburg (DE)

(73) Assignee: Fette GmbH, Schwarzenbek (DE)

( * ) Notice: Subject to any disclaimer, the term of this patent is extended or adjusted under 35 U.S.C. 154(b) by 422 days.

(21) Appl. No.: 12/566,187

(22) Filed: Sep. 24, 2009

(65) Prior Publication Data

US 2010/0078841 A1 Apr. 1, 2010

(30) Foreign Application Priority Data

Sep. 25, 2008 (DE) .......................... 10 2008 049 015

(51) Int. Cl.
*B29C 45/76* (2006.01)

(52) U.S. Cl.
USPC .......................... 264/40.1; 425/145; 425/150

(58) Field of Classification Search
USPC .................................. 264/40.1; 425/145, 150
See application file for complete search history.

(56) References Cited

U.S. PATENT DOCUMENTS

| 5,977,780 A | 11/1999 | Herrmann |
| 2004/0012781 A1 | 1/2004 | Gehrlein |
| 2005/0184435 A1* | 8/2005 | Hinzpeter et al. ............ 264/409 |
| 2011/0093212 A1 | 4/2011 | Herrmann et al. |

FOREIGN PATENT DOCUMENTS

| DE | 10 2004 008 321 B3 | 11/2005 |
| EP | 0 468 023 B1 | 2/1991 |
| EP | 0 908 718 B1 | 8/1998 |
| EP | 0889321 B1 | 12/1998 |
| EP | 1568480 | 8/2005 |
| EP | 1669755 | 6/2006 |
| EP | 1844924 | 10/2007 |

OTHER PUBLICATIONS

"In situ monitoring and control of moisture content in pharmaceutical powder processes using an open-ended coaxial probe" by Gradinarsky et al. (Meas. Sci. Technol. 17(2006) 1847-1853).*

* cited by examiner

*Primary Examiner* — Yogendra Gupta
*Assistant Examiner* — John Robitaille
(74) *Attorney, Agent, or Firm* — Vidas, Arrett & Steinkraus, P.A.

(57) ABSTRACT

A method for quality surveillance of powdered press material for a rotary press, in which the press material is fed from a reservoir via a preferably vertical feed channel to a filling device, which continuously fills dies of a rotor with press material wherein to the feed channel and/or the filling device is assigned a microwave resonator with an analysis unit, which measures the moisture and/or the density and/or the size of the granules of the press material, and at least one press variable of the microwave resonator is used for changing a control variable of the rotary press.

8 Claims, 2 Drawing Sheets

ROTARY PRESS FOR QUALITY SURVEILLANCE OF POWDERED PRESSED MATERIAL

CROSS-REFERENCE TO RELATED APPLICATIONS

Not applicable.

STATEMENT REGARDING FEDERALLY SPONSORED RESEARCH

Not applicable.

BACKGROUND OF THE INVENTION

Rotary presses serve, as is generally known, for producing tablet shaped pellets, in particular, for the pharmaceutical industry. Rotary presses have largely the same construction. A rotationally driven rotor contains upper and lower punches and dies, into which powdered press material is filled continuously with the use of a filling device, and the powdered material is compressed using the press punches. The press punches are actuated using pressure rollers. Outside of the press stations, the press punches are controlled by control cams. After pressing, the pellets are ejected using the lower punches, and removed from a deflector.

In the pharmaceutical sector, in particular, the pellets must meet a series of quality criteria, for example, weight, strength, break resistance, height, active substance content, active substance release, dispersal, friability, porosity, surface, moisture content, etc. It is known to perform quality surveillance through sampling during production. If the tested pellets do not correspond to the desired conditions, appropriate setting parameters in the press are changed. Setting parameters are, for example, the rotational speed of the rotor, the rotational speed of the filling device, the powder dosing into the dies, the pressing force over the pressure rollers, etc.

Online process control is also known. A test device is positioned directly alongside the tablet press. Samples are automatically removed from the tablet flow and guided to the testing device. There, the pellets are isolated and measured. A change of at least one setting parameter of the lower press occurs via a computer interface from the testing device to the machine control. It is generally known to assign to such rotary presses a machine computer and a workstation which perform the control and regulation of the pressing operation.

It is also known to directly test, during the production, the pressing force to which a pellet is subjected. As is known, the pressing force is a measure for the tablet weight and tablet hardness. If the pressing force does not have the required value, for example, either the quantity of powder supplied per die and/or the setting of the pressure rollers is changed.

Finally, it is also known, for example, to measure the active substance in the pellets using a near infrared spectroscopy (NIR), or a laser fluorescence spectroscopy (LIF). Such a measurement can take place within the housing of the tablet press, either after the dies are filled, or during the ejection of the pellets from the dies.

It is the objective of the invention to specify a method for quality surveillance of pressed material in a rotary press, using which a rapid response to production changes is possible, and the loss ratio of pellets with insufficient quality features can be minimized.

BRIEF SUMMARY OF THE INVENTION

With the method according to the invention, a microwave resonator with an analysis unit is assigned to the feed channel and/or the filling device; the analysis unit measures the moisture and/or density and/or the size of the granules of the press material. At least one measured variable of the microwave resonator is used for changing one of the control variables of the rotary press.

Using the method according to the invention, a process optimization occurs because the powder to be checked is measured already in the feed area, before it is filled into the dies. It is measured with regard to its moisture and/or density and/or granule size. This permits a faster reaction to production changes, and the loss ratio of tablets with improper quality characteristics can be reduced. As is generally known, powder batches supplied to the rotary presses can differ with regard to moisture, density, and granule size, so that appropriate measures can be performed, such as regulating activities or stopping the press, before further tablets are pressed.

Moisture, density and granule size of the press powder have an influence on the flow behavior of the powder as well as on the quality criteria of the pellets, such as weight, dispersal, friability, porosity and moisture. With the method according to the invention using the measurement results, statistical variables, for example, average values and/or standard deviations can be calculated, and/or displayed, and/or recorded in the machine computer and/or in the workstation. In the case of deviations from the specified limit ranges of the powder state, the production of the rotary press is stopped by the machine computer and/or the workstation. Alternatively, at least one closed control loop can be activated in order to adjust the press to the changed powder state. According to an embodiment of the invention, the rotational speed of the rotor, the rotational speed of the filling device, the powder dosing into the dies, the change of pressing force by means of pressure roller adjustment, etc. serve as control variables. These control variables can be changed using the available computer system. Alternatively, a manual adjustment can also be performed.

Microwave resonators are generally known. EP 0 468 023 B1, the entire contents is incorporated herein by reference, describes the measurement of two resonance parameters for density independent moisture measurements. EP 0 908 718 B1, the entire contents is incorporated herein by reference, describes a stray field sensor for density and moisture measurement. From EP 0 889 321 B1, the entire contents is incorporated herein by reference, it is known to measure the moisture and the density of a strand, for example, a tobacco rod using such resonators.

Using a microwave resonator a density independent moisture measurement is possible with the invention, as well as a moisture independent density measurement. Furthermore, the granules can be analyzed with respect to its grain size.

In a rotary press according to the invention according to Claim 8, a microwave resonator with an analysis unit is assigned to a feed for a filling device, or to a filling device. Usually, the press powder is fed to the filling device from a reservoir above the press via an appropriate down channel. The microwave resonator, for example, a hollow space or stray field resonator, can be assigned to such a feed within, or outside of the housing of the press. Alternatively, the microwave resonator can also be disposed on the wall of the filling device, wherein however, the assignment to the feed is preferable because more space is available for the attachment of the microwave resonators.

It is known to change individual control variables of the rotary press using control or regulation. Thus, for instance, the fill depth in the die is determined by the adjustment of the lower punches in the dies. This setting, in turn, is determined by a filling cam, which can be adjusted in its height using a control device. The relative position of the pressure rollers to the press punches can also be changed, similarly, using a suitable adjustment device. The pressing force created by the pressure rollers can be measured, and serves as an actual value to a regulation. The position of the filling cam can also be an actual value to a regulation. By changing the target values in such regulations, the individual parameters of the pellet can be influenced. If, using the microwave resonator, it is determined that the supplied press material has changed in its conditions, in particular, in its moisture, density and/or grain size, it is possible to respond to this with appropriate control variables of the rotary press. If the measured values in the press material deviate too greatly from the specified values, a stop of the rotary press can also be initiated, in order to prevent the production of deficient pellets.

BRIEF DESCRIPTION OF THE VIEWS OF THE DRAWINGS

In the following, the invention is explained in more detail using drawings.

DETAILED DESCRIPTION OF THE INVENTION

Figure 1:
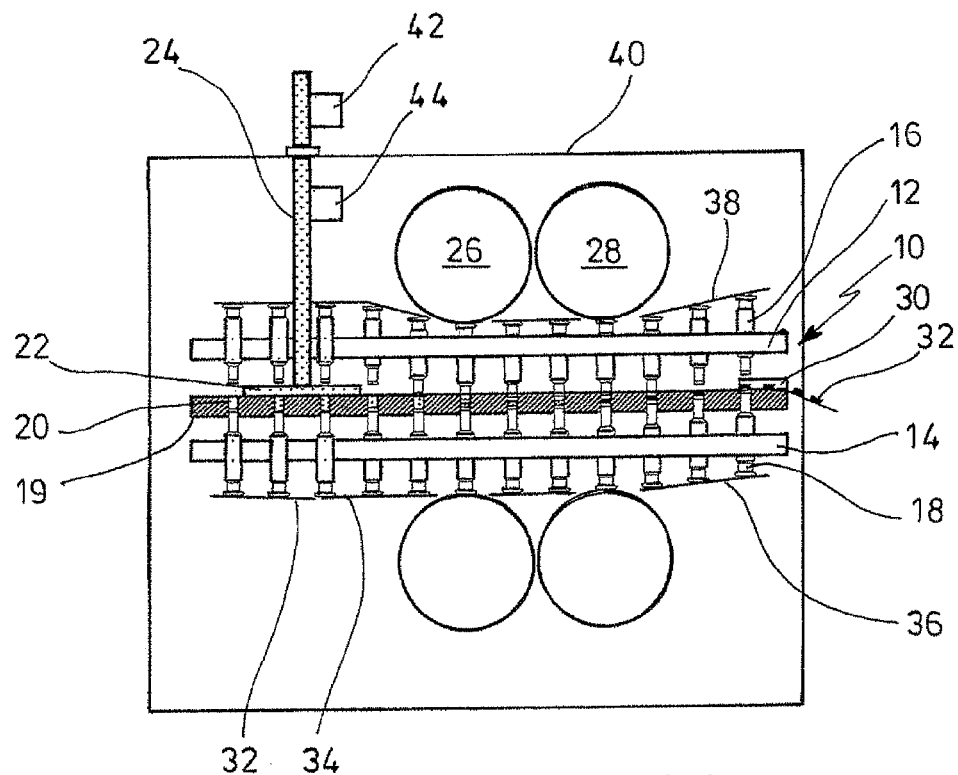
FIG. 1 shows a schematic representation of a rotary press according to the invention.

While this invention may be embodied in many different forms, there are described in detail herein a specific preferred embodiment of the invention. This description is an exemplification of the principles of the invention and is not intended to limit the invention to the particular embodiment illustrated The rotary press represented in FIG. 1 has a rotor 10, which contains an upper guide 12 and a lower guide 14 for upper punches 16 and lower punches 18. A die disk 19 with dies 20 is located in between. A filling device 22 serves for filling the dies 20 with press material. The filling device 22 is connected to a vertical feed channel 24, via which press material is fed from a reservoir, not shown, to the filling device 22.

A press station with an upper and lower preliminary pressure rollers 26 and upper and lower main pressure rollers 28 is located in the peripheral area to the filling station. The pressure roller pairs 26, 28 can be adjusted in their distance to the die disk 19 through an appropriate adjustment device, not shown.

To the die disk 19 is also assigned a deflector 30, via which the pellets 32 are led away.

The press punches 16, 18 are guided by suitable guide cams. In the area of the filling device 22, a lower filling cam 32 is provided, and in connection to it a dosing cam 34, which determines the volume accepted by the dies 20. An ejector cam 36 effects the lifting of the lower punch for ejecting the pellets 32. An upper guide cam 38 serves behind the press station for lifting the upper punches 16 after the pressing. The described arrangements and functions are generally known.

The described components are disposed within a housing 40. The feed channel 24 is guided through the upper wall of the housing 40.

It can be recognized that a microwave resonator 42 is disposed outside of the housing. As an alternative, as shown with 44, it can also be disposed within the housing 40. Here, this is a so-called stray field resonator, which is disposed on the wall of the feed channel 24. Using the microwave resonator 42 or 44, the density and/or the moisture and/or the grain size of the granules of powder can be determined.

Figure 2:
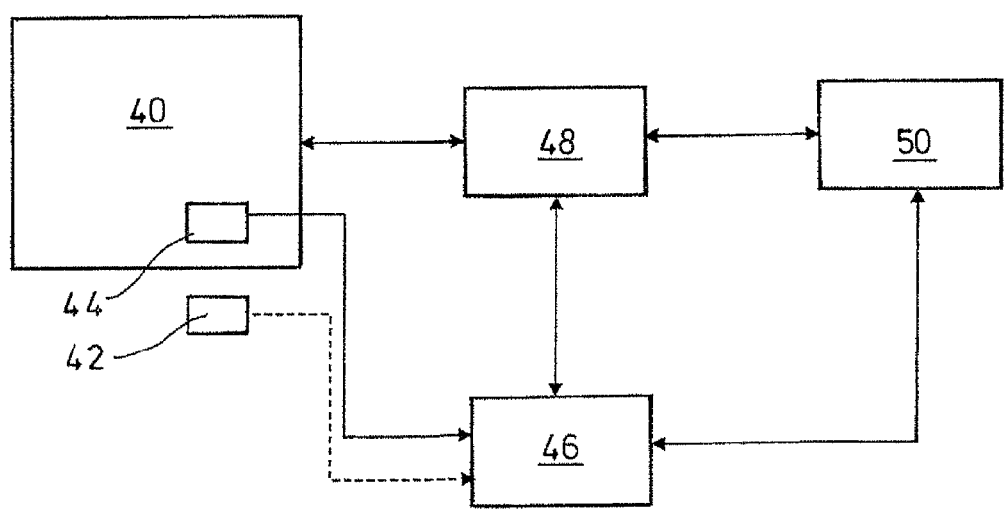
FIG. 2 shows a simple block diagram for the method according to the invention.

FIG. 2 shows only the housing 40 of the rotary press according to FIG. 1. It further represents the resonators 42 and 44, which are connected to analysis electronics 46. The electronics are connected to a machine computer 48 or workstation 50 for the tablet press. Therefore, using the resonators 42 or 44, it is possible to influence control variables of the rotary press, in particular, the rotational speed of the rotationally driven rotor, rotational speed of the rotor in the filling device 22, setting of the dosing or filling cams 32, 34, setting of the pressure rollers 26 and 28. In the analysis electronics 46, the measurement value for the density, moisture and/or grain size is determined, and converted into an actual value, which can be provided to a regulation for producing the mentioned control variables. In the machine computer or workstation 48, 50, the measurement results can also be used to calculate and/or to display and/or to record statistical variables, such as the average values and/or standard deviation. If specified limit ranges of the press material are exceeded, the tablet press can also be stopped.

Figure 3:
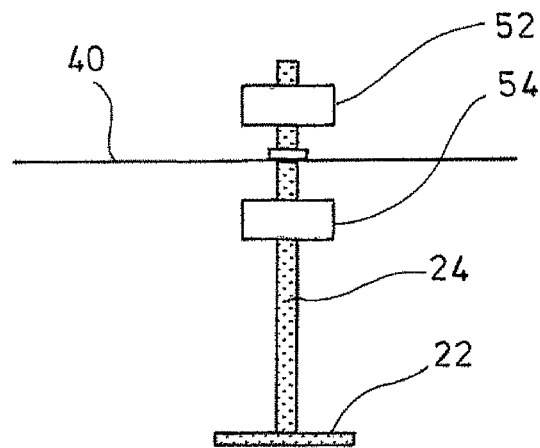
FIG. 3 shows details for the rotary press according to FIG. 1 in an alternative embodiment.

An alternative to FIG. 1 is represented in FIG. 3. In FIG. 3, a hollow space resonator 52 and 54 surrounds the feed channel 24 outside of, or inside of the housing 40.

Figure 4:
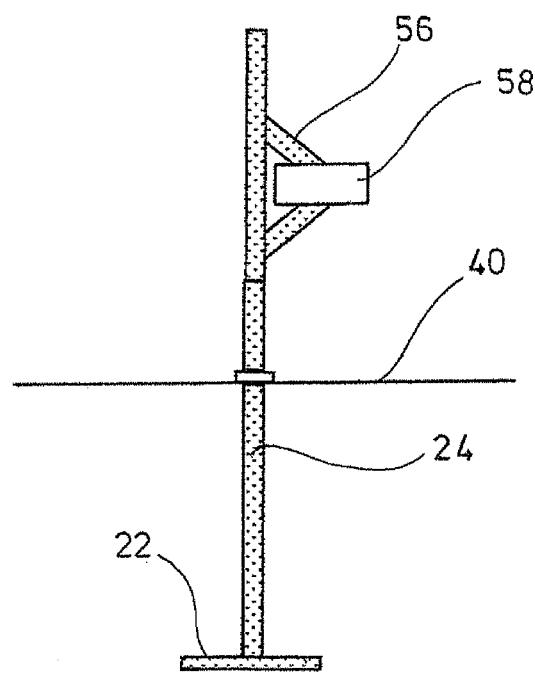
FIG. 4 shows a further alternative embodiment to FIG. 1.

A further alternative is represented in FIG. 4. Outside of the housing 40, the feed channel 24 has a bypass channel 56, which is surrounded by a hollow space resonator 58. From the main flow in the feed channel 24, an auxiliary flow branches into the bypass channel 56, and its content is measured with the hollow space resonator 58 regarding the mentioned variables. The material from the auxiliary flow is fed back into the main flow in the feed channel 24.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A rotary press with a housing and a rotor with dies and upper and lower press punches, guide cams for the press punches, pressure rollers, and a filling device in the housing, and a feed for powdered press material to the filling device, characterized in that to the feed (24) or the filling device (22) is assigned a microwave resonator for measuring the density and/or the size of the granulate of the powder including an analysis unit (46) receiving the measured values from the microwave resonator, and in that a control device changes the rotation speed of the rotor and/or the rotational speed of the filling device and/or the adjustment for a dosing curve and/or adjustment for the pressure rollers if an actual value representing a measured value of the microwave resonator differs from a predetermined desired value.

2. A rotary press according to claim 1, characterized in that the microwave resonator (42, 44) is connected to a machine computer (48) and/or a workstation (50) of the rotary press.

3. The rotary press according to claim 1, characterized in that the microwave resonator (42) is disposed outside or inside the housing (40).

4. The rotary press according to claim 1, characterized in that the microwave resonator is a stray field resonator (42, 44) is disposed in the wall of the feed channel (24) or the filling device.

5. The rotary press according to claim 1, characterized in that a hollow space resonator (52, 54) surrounds a feed channel.

6. The rotary press according to claim 4, characterized in that a bypass channel (56) is assigned to the feed channel, and the microwave resonator (58) is assigned to the bypass channel (56).

7. The rotary press according to claim 1, characterized in that a control device is provided for the rotational speed of the rotor and/or the rotational speed of the filling device (22) and/or an adjustment device for a dosing cam (34) and/or an adjustment device for the pressure rollers (26, 28), and a proportional actual value of the measured variable of the microwave resonator is supplied to the control device.

8. A rotary press comprising:
a housing;
a rotor with dies and upper and lower press punches;
guide cams for the press punches;
pressure rollers;
a filling device in the housing;
a feed for powdered press material to the filling device, and a microwave resonator with an analysis unit is assigned to the feed and/or the filling device for measuring the density and/or the size of the granulate of the powder receiving the measured values from the microwave resonator, and in that a control device changes the rotation speed of the rotor and/or the rotational speed of the filling device and/or the adjustment for a dosing curve and/or adjustment for the pressure rollers if an actual value representing a measured value of the microwave resonator differs from a predetermined desired value.

* * * * *